(12) United States Patent
Melnicky et al.

(10) Patent No.: US 8,129,421 B2
(45) Date of Patent: Mar. 6, 2012

(54) METHOD FOR PREPARING 4-[3,5-BIS(2-HYDROXYPHENYL)-[1,2,4] TRIAZOL-1-YL]-BENZOIC ACID

(75) Inventors: Radek Melnicky, Sternberk (CZ); Pavel Hradil, Hlusovice (CZ); Lubomir Kvapil, Slatinice (CZ); Martin Grepl, Hlusovice (CZ); Petr Slezar, Olomoue (CZ)

(73) Assignee: Farmak, A S, Olomouc (CZ)

( * ) Notice: Subject to any disclaimer, the term of this patent is extended or adjusted under 35 U.S.C. 154(b) by 1 day.

(21) Appl. No.: 12/864,907

(22) PCT Filed: Jun. 16, 2008

(86) PCT No.: PCT/CZ2008/000068
§ 371 (c)(1),
(2), (4) Date: Oct. 12, 2010

(87) PCT Pub. No.: WO2009/094956
PCT Pub. Date: Aug. 6, 2009

(65) Prior Publication Data
US 2011/0034702 A1 Feb. 10, 2011

(30) Foreign Application Priority Data
Jan. 30, 2008 (CZ) ................................. PV 2008-49

(51) Int. Cl.
*A61K 31/41* (2006.01)
*C07D 249/08* (2006.01)
(52) U.S. Cl. ..................................... 514/383; 548/262.2
(58) Field of Classification Search .................. 514/383; 548/262.2
See application file for complete search history.

(56) References Cited

FOREIGN PATENT DOCUMENTS
WO  WO 97/49395      12/1997
WO  WO 97/49395 A  * 12/1997
WO  WO 03/053986      7/2003

OTHER PUBLICATIONS
Steinhauser S. et al., Complex formation of ICL670 and related ligands with $Fe^{III}$ and $Fe^{II}$, European Journal of Inorganic Chemostry, Wiley-VCH VERLAG, Weinheim, DE, No. 21, Jan. 1, 2004, pp. 4177-4192.
Brunetti H. et al., Die Synthesis von asymmetrisch substituierten o-Hydroxyphenyl-s-triazinen, Helvetica Chimica Acta, 1972, p. 1566-1595, vol. 55.
International Search Report for International application No. PCT/CZ2008/000068, Date of Mailing: Jun. 10, 2009.

* cited by examiner

*Primary Examiner* — Susannah Chung
(74) *Attorney, Agent, or Firm* — Pearl Cohen Zedek Latzer, LLP

(57) ABSTRACT

A method for preparing 4-[3,5-bis(2-hydroxyphenyl )-[1,2, 4]triazol-1-yl]benzoic acid of formula (I) by reaction of 2-(2-hydroxyphenyl)benz[e][1,3]oxazin-4-one of formula (II) with 4-hydrazinobenzoic acid of formula (III) in an organic acid or in a mixture of an organic acid and an organic solvent.

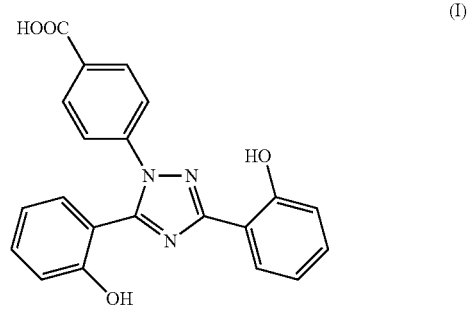

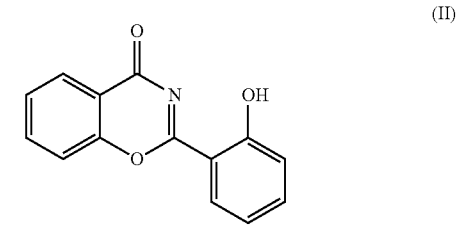

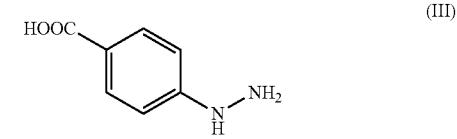

4 Claims, No Drawings

METHOD FOR PREPARING 4-[3,5-BIS(2-HYDROXYPHENYL)-[1,2,4] TRIAZOL-1-YL]-BENZOIC ACID

CROSS-REFERENCE TO RELATED APPLICATIONS

This application is a National Phase Application of PCT International Application No. PCT/CZ2008/000068, International Filing Date Jun. 16, 2008, entitled "A METHOD FOR PREPARING 4-[3,5-BIS(2-HYDROXYPHENYL)-[1,2,4] TRIAZOL-1-YL]BENZOIC ACID", published on Aug. 6, 2009 as International Publication Number WO 2009/094956, which claims priority of Czech Patent application No. PV 2008-49, filed Jan. 30, 2008, both of which are incorporated herein by reference in their entirety.

TECHNICAL FIELD

The invention deals with a new method of preparation of 4-[3,5-bis(2-hydroxyphenyl)[1,2,4]-triazol-1-yl]-benzoic acid of formula I,

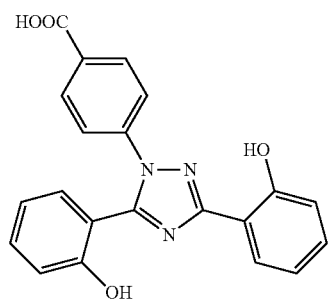

(I)

which is known as deferasirox and is used, in the form of free acid or its salt, to reuptake excess trivalent metals from body tissues. It is used to treat haemosiderosis (iron overload) and diseases caused by excess aluminium (dialysis encephalopathy, osteomalacy and Alzheimer disease).

BACKGROUND ART

So far, several methods of preparation of deferasirox of formula I have been described, which are listed in CZ patent No. 291470 based on WO 97/49395.

Method (a): Condensation reaction of benzoxazinone of formula II

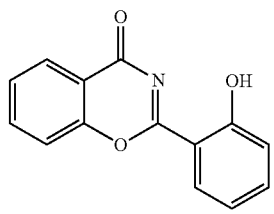

(II)

with 4-hydrazinobenzoic acid of formula III

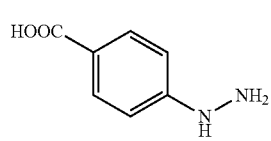

(III)

in polar solvents or mixtures of solvents, preferably in lower alcohols, with optional addition of a base if 4-hydraziobenzoic acid hydrochloride is used for the reaction under cooling conditions, at room temperature or at increased temperature up to the boiling temperature of the reaction mixture.

The starting compound of formula II can be prepared, for example, through a reaction of salicylic acid with salicylamide in the presence of thionyl chloride (Brunetti H., Lüthi C. E., Helvetica Chimica Acta, 55, 1566 (1972)).

Method (b): Reaction of 1,2,4-dithiazolidine of formula IV with 4-hydrazinobenzoic acid of formula III without a solvent or in a polar solvent or their mixtures under cooling conditions, at room temperature or at increased temperature.

(IV)

Method (c): Reaction of the amide of formula V with 4-hydrazinobenzoic acid of formula III in a polar protic solvent under slightly acidic catalysis.

(V)

The above-mentioned methods of preparation suffer from the drawback of generating high quantities of impurities that decrease the yield of the reaction and impair the quality of the prepared deferasirox.

Since there are not given any yields or purities in the Examples of WO 97/49395, we have carried out several times thorough reproduction of Example 5. In the best case the yield of 57% and HPLC purity of 97% could be obtained; in a further attempt the yield was 68% but the purity was only 63% HPLC.

DISCLOSURE OF INVENTION

The above-mentioned disadvantages can be overcome by the method of the invention, which is a method of preparing 4-[3,5-bis(2-hydroxyphenyl)[1,2,4]triazol-1-yl]benzoic acid of formula I

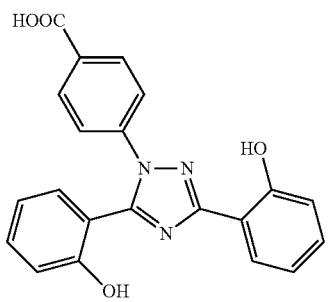

by reaction of 2-(2-hydroxyphenyl)benz[e][1,3]oxazin-4-one of formula II

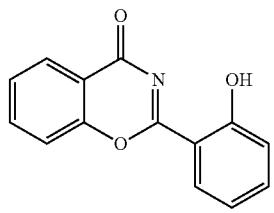

with 4-hydrazinobenzoic acid of formula III

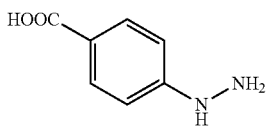

The essence of the invention consists in carrying the reaction out in an organic acid or in a mixture of an organic acid and an organic solvent.

Another aspect of the invention comprises using:

a $C_1$ to $C_4$ carboxylic acid, or a $C_1$ to $C_4$ carboxylic acid that may be substituted in the chain with one or more atoms of a halogen, hydroxy group or alkoxy group, as the organic acid.

In another aspect of the invention the organic solvent is a solvent from the group including aromatic hydrocarbons, chlorinated solvents, ethers, esters and polar aprotic solvents.

Still another aspect of the invention comprises carrying the reaction out in the equimolar quantity or in a slight excess of 4-hydrazinobenzoic acid of formula III.

The reaction can be preferably carried out at temperatures from 20 to 160° C., more preferably at the boiling temperature of the reaction mixture.

The reaction can be preferably carried out for 0.5 to 3 hours.

For example, the following organic acids can be used formic acid, acetic acid, propionic acid or butyric acid; trifluoroacetic acid, dichloroacetic acid;
lactic acid;
methoxyacetic acid, methoxypropionic acid.

The following organic solvents can be used, for example, aromatic solvents, e.g. toluene, xylene or ethylbenzene; chlorinated solvents, e.g. chlorobenzene;
polar aprotic solvents, e.g. dimethylformamide, dimethylacetamide, N-methylpyrrolidone, 1,3-dimethylimidazolidinedione, acetonitrile;
ethers, e.g. 2-methyltetrahydrofuran, diisopropyl ether, dibutyl ether;
esters, e.g. ethyl acetate.

As the purifying operation, precipitation or crystallization from alcohols, suitably from lower alcohols, e.g. methanol, can be used.

Advantages of the method of the invention are as follows:
The reaction temperature is mild and does not require tedious control, as the reaction preferably occurs at boiling temperature
The reaction time is short, preferably 0.5 to 3 hours;
Under optimum conditions both the purity of the substance and yield are high.

EXAMPLES

The essence of the method of the invention is explained in a more detailed way in the following examples. These examples are of an illustrative nature only and should in no case limit the scope of the invention.

Example 1

A suspension of 10.65 g (44.5 mmol) of 2-(2-hydroxyphenyl)benz[e][1,3]oxazin-4-one, 7.97 g (52.4 mmol) of 4-hydrazinobenzoic acid and 57.0 ml of propionic acid is heated to the boiling temperature of the reaction mixture and is kept at this temperature (132° C.) for 2 hours. After completion of the reaction, 57 ml of ethyl acetate is added to the suspension after cooling and the suspension is stirred for 30 minutes.

The resulting crystalline product is filtered, washed with 30 ml of ethyl acetate on the filter and dried to a constant weight. A white crystalline product weighing 14.38 g is obtained, i.e. 87% of the theory, with HPLC purity above 99.4% and a melting temperature of 260 to 265° C.

Precipitation of the raw product is performed in such a way that the raw product is dissolved in a sodium hydroxide solution (6.16 g in 60 ml of water) and extraction with 50 ml of ethyl acetate is carried out. After separation the aqueous layer is filtered with 0.5 g of active carbon and after filtration the solution is acidified with hydrochloric acid to pH=1 to 2 and the resulting suspension is stirred at the temperature of 20° C. for 30 minutes. The precipitated product is aspirated and washed with water until neutral pH. After drying to a constant weight, 14.3 g are obtained, i.e. 86% of the theory, with an HPLC purity above 99.8% and melting temperature of 263 to 265° C.

The precipitated product is stirred up with ethyl acetate by stirring in a suspension with 57 ml of ethyl acetate at a temperature of 20° C. for 30 minutes. The stirred-up product is aspirated and washed with ethyl acetate. After drying to a constant weight, 13.56 g are obtained, i.e. 82% of the theory, with HPLC purity above 99.8%. Melting temperature: 264 to 266° C.

Example 2

A suspension of 0.7 g (2.93 mmol) of 2-(2-hydroxyphenyl) benz[e][1,3]oxazin-4-one and 0.52 g (3.44 mmol) of 4-hydrazinobenzoic acid in 8.0 ml of toluene and 5 ml of propionic acid is heated to its boiling point and is maintained at this temperature (110° C.) for 2 hours. After completion of the reaction, the reaction mixture is cooled and filtration is carried out. The crystalline product is washed with toluene and dried until dry.

0.95 g of white product is obtained (87% of the theory), which contains 97.1% of deferasirox having a melting temperature of 256 to 263° C.

Precipitation of the raw product is performed in such a way that raw deferasirox is dissolved in a solution of 0.6 g of sodium hydroxide in 30.0 ml of water and the solution is extracted with ethyl acetate (1×30.0 ml). The aqueous phase is filtered with active carbon and the filtrate is acidified with concentrated hydrochloric acid until pH=1 to 2. The suspension is stirred at the temperature of 20° C. for 1 hour and the precipitated product is filtered and washed with water. After drying, 0.73 g of precipitated deferasirox (67% of the theory) is obtained with a purity of 98.5% and a melting temperature of 260 to 264° C.

Example 3

A suspension of 0.7 g (2.92 mmol) of 2-(2-hydroxyphenyl) benz[e][1,3]oxazin-4-one and 0.52 g (3.44 mmol) of 4-hydrazinobenzoic acid in 8 ml of 2-methyltetrahydrofuran and 5 ml of propionic acid is heated to its boiling point and maintained at this temperature (98° C.) for 2 hours. After completion of the reaction, the mixture is cooled and filtered. The product is washed with 2-methyltetrahydrofuran. After drying, 0.55 g of raw deferasirox is obtained, i.e. 50% of the theory, with an HPLC purity of 95.3% and a melting temperature of 255 to 262° C.

Example 4

A suspension of 0.7 g (2.92 mmol) of 2-(2-hydroxyphenyl) benz[e][1,3]oxazin-4-one and 0.52 g (3.44 mmol) of 4-hydrazinobenzoic acid in 8 ml ethyl acetate and 5.0 ml of propionic acid is heated to its boiling point and maintained at this temperature (92° C.) for 2 hours. After completion of the reaction, the mixture is cooled and filtered. The product is washed with ethyl acetate. After drying, 0.92 g of raw deferasirox is obtained, i.e. 84% of the theory, with an HPLC purity of 99.7% and a melting temperature of 258 to 263° C.

Example 5

A suspension of 0.7 g (2.92 mmol) of 2-(2-hydroxyphenyl) benz[e][1,3]oxazin-4-one and 0.52 g (3.44 mmol) of 4-hydrazinobenzoic acid in 5 ml of lactic acid is heated to its boiling point and maintained at this temperature (115° C.) for 2 hours. After completion of the reaction the mixture is cooled down, causing separation of the crystalline product. 5 ml of ethyl acetate are added. After drying, 0.53 g of raw deferasirox is obtained, i.e. 49% of the theory, with an HPLC content of 94% and a melting temperature of 248 to 260° C.

Precipitation of the raw product is performed in such a way that raw deferasirox is dissolved in a solution of 0.23 g of sodium hydroxide in 20.0 ml of water and the solution is extracted with ethyl acetate (1×20.0 ml). The aqueous phase is filtered with active carbon and the filtrate is acidified with 0.75 ml of concentrated hydrochloric acid until pH=1 to 2. The suspension is stirred at a temperature of 20° C. for 1 hour and the precipitated product is filtered and washed with water. After drying, 0.31 g of precipitated deferasirox is obtained, i.e. 29% of the theory, with a purity of 98.5% and a melting temperature of 261 to 264° C.

The precipitated product is stirred up in ethyl acetate by stirring in a suspension with 10 ml of ethyl acetate at a temperature of 20° C. for 30 minutes. The stirred-up product is aspirated and washed with ethyl acetate. After drying to a constant weight, 0.19 g is obtained, i.e. 17% of the theory, with a purity above 99.0%. Melting temperature: 258 to 263° C.

Example 6

A suspension of 0.7 g (2.92 mmol) of 2-(2-hydroxyphenyl) benz[e][1,3]oxazin-4-one and 0.52 g (3.44 mmol) of 4-hydrazinobenzoic acid in 5 ml of N,N-dimethylformamide and 5 ml of propionic acid is heated up to 150° C. The mixture is maintained at this temperature and stirred for 1.5 hours. After completion of the reaction, the mixture is cooled and poured onto crushed ice. The resulting crystals are aspirated and washed with water. After drying, 0.88 g of raw deferasirox is obtained, i.e. 81% of the theory, with an HPLC purity of 93% and a melting temperature of 255 to 262° C.

Example 7

A suspension of 0.7 g (2.92 mmol) of 2-(2-hydroxyphenyl) benz[e][1,3]oxazin-4-one and 0.52 g (3.44 mmol) of 4-hydrazinobenzoic acid in 5 ml of N-methylpyrrolidone and 5 ml of propionic acid is heated to 120° C. The mixture is maintained at this temperature and stirred for 1 hour. After completion of the reaction, the mixture is cooled and poured onto crushed ice. The resulting crystals are aspirated and washed with water. After drying, 0.99 g of raw deferasirox is obtained, i.e. 91% of the theory, with an HPLC content of 92.9% and a melting temperature of 250 to 261° C.

Example 8

A suspension of 0.7 g (2.92 mmol) of 2-(2-hydroxyphenyl) benz[e][1,3]oxazin-4-one and 0.52 g (3.44 mmol) of 4-hydrazinobenzoic acid in 5 g of trichloroacetic acid and 5 ml of toluene is heated to 110° C. The mixture is maintained and stirred at this temperature for 3 hours. After completion of the reaction, the mixture is cooled and poured onto crushed ice. The resulting crystals are aspirated and washed with water and ethyl acetate. After drying, 0.6 g of raw deferasirox is obtained, i.e. 55% of the theory, with an HPLC content of 99.56% and a melting temperature of 258 to 262° C.

Example 9

A suspension of 0.7 g (2.92 mmol) of 2-(2-hydroxyphenyl) benz[e][1,3]oxazin-4-one and 0.52 g (3.44 mmol) of 4-hydrazinobenzoic acid in 5 ml of methoxypropionic acid is heated to 100° C. The mixture is maintained and stirred at this temperature for 1 hour. After completion of the reaction, the mixture is cooled and 5 ml of ethyl acetate are added. The resulting mixture is stirred for 10 minutes, then it is filtered and the crystals are washed with ethyl acetate. After drying, 0.66 g of raw deferasirox is obtained, i.e. 60% of the theory, with an HPLC content of 99.3% and a melting temperature of 259 to 263° C.

Example 10

A suspension of 0.7 g (2.92 mmol) of 2-(2-hydroxyphenyl)benz[e][1,3]oxazin-4-one and 0.52 g (3.44 mmol) of 4-hydrazinobenzoic acid in 5 ml of propionic acid and 5 ml of chlorobenzene is heated to 130° C. The mixture is maintained and stirred at this reflux temperature for 1 hour. After completion of the reaction, the mixture is cooled and poured onto crushed ice.

The mixture is alkalized with sodium hydroxide until pH=11 and extracted with 20 ml of ethyl acetate. After separation of the layers, the aqueous phase is filtered with active carbon and acidified with concentrated hydrochloric acid until pH=1 to 2. The resulting suspension is stirred for 10 minutes and then it is filtered and the crystals are washed with water. After drying, 1.01 g of precipitated deferasirox is obtained, i.e. 93% of the theory, with an HPLC content of 95.41% and a melting temperature of 253 to 262° C.

Example 11

Purifying Operation

A mixture of 1.01 g (2.71 mmol, 99.45% HPLC) of deferasirox in 50 ml of methanol is dissolved at the boiling temperature. 0.2 g of active carbon is added to the solution and filtration is performed, after 15 minutes. The filtrate is concentrated to achieve crystallization. The crystals, obtained by cooling, are aspirated and washed with 10 ml of methanol. After drying, 0.74 g of re-crystallized deferasirox is obtained, i.e. 74% of the theory, with an HPLC content of 99.9% and a melting temperature of 264 to 266° C.

Industrial Applicability

The method of preparation of 4-[3,5-bis(2-hydroxyphenyl)[1,2,4]triazol-1-yl]benzoic acid of formula I according to the invention can be applied in favourable technological and economical conditions while maintaining high yields even under mild reaction conditions.

The invention claimed is:

1. A method for preparing 4-[3,5-bis(2-hydroxyphenyl)-[1,2,4]triazol-1-yl]benzoic acid of formula I

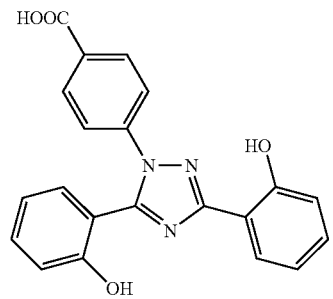

by reaction of 2-(2-hydroxyphenyl)benz[e][1,3]oxazin-4-one of formula II

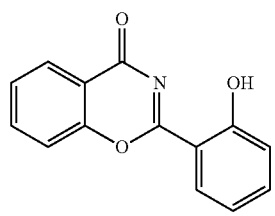

with 4-hydrazinobenzoic acid of formula III

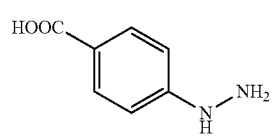

wherein the reaction is carried out in propionic acid or a mixture of propionic acid and an organic solvent.

2. The method according to claim 1, wherein the organic solvent used is selected from the group including aromatic hydrocarbons and esters.

3. The method according to claim 1, wherein the reaction is carried out at temperatures from 20 to 160 ° C.

4. The method according to claim 1, wherein the reaction is carried out for 0.5 to 3 hours.

* * * * *